tent No.: US 9,345,560 B2
(45) Date of Patent: May 24, 2016

(12) United States Patent
Rovelló Montalbán

(54) METAL PILLAR FOR DENTAL IMPLANTS

(71) Applicant: Joaquín Rovelló Montalbán, Barcelona (ES)

(72) Inventor: Joaquín Rovelló Montalbán, Barcelona (ES)

( * ) Notice: Subject to any disclaimer, the term of this patent is extended or adjusted under 35 U.S.C. 154(b) by 0 days.

(21) Appl. No.: 14/654,856

(22) PCT Filed: Dec. 27, 2013

(86) PCT No.: PCT/ES2013/000282
§ 371 (c)(1),
(2) Date: Jun. 23, 2015

(87) PCT Pub. No.: WO2014/102408
PCT Pub. Date: Jul. 3, 2014

(65) Prior Publication Data
US 2015/0335402 A1    Nov. 26, 2015

(30) Foreign Application Priority Data
Dec. 26, 2012    (ES) .............................. 201231362 U

(51) Int. Cl.
*A61C 8/00*    (2006.01)
(52) U.S. Cl.
CPC .............. *A61C 8/0074* (2013.01); *A61C 8/006* (2013.01)
(58) Field of Classification Search
CPC .... A61C 8/005; A61C 8/0051; A61C 8/0054; A61C 8/0056; A61C 8/0059; A61C 8/0069; A61C 8/0072; A61C 8/0074
See application file for complete search history.

(56) References Cited

U.S. PATENT DOCUMENTS

| 5,030,095 | A | * | 7/1991 | Niznick | A61C 8/005 433/173 |
| 5,052,929 | A | * | 10/1991 | Seal | A61C 8/005 433/173 |
| 5,092,771 | A | * | 3/1992 | Tatum, III | A61C 8/0018 433/173 |
| 5,316,477 | A | * | 5/1994 | Calderon | A61C 8/0069 433/172 |
| 6,824,386 | B2 | * | 11/2004 | Halldin | A61C 8/0001 433/173 |
| 7,632,095 | B2 | * | 12/2009 | Ostman | A61C 5/08 433/172 |
| 8,651,865 | B2 | * | 2/2014 | Badia | A61C 8/005 206/368 |
| 2004/0043360 | A1 | * | 3/2004 | Obata | A61C 8/005 433/173 |
| 2007/0082320 | A1 | * | 4/2007 | Faus Badia | A61C 8/005 433/173 |
| 2010/0151421 | A1 | | 6/2010 | Devengencie et al. | |
| 2010/0266986 | A1 | * | 10/2010 | Faus Badia | A61C 8/005 433/173 |

FOREIGN PATENT DOCUMENTS

ES    2205504 T3    5/2004
ES    2315060 A1    3/2009

* cited by examiner

*Primary Examiner* — Ralph Lewis
(74) *Attorney, Agent, or Firm* — Richard M. Goldberg

(57) ABSTRACT

A one-piece, angled metal pillar for dental implants, includes a lower base with a threaded shank, a smooth cylindrical segment having one end connected with one end of the lower base, a bevel shaped as a frustoconical support base having one end connected to an opposite end of the smooth cylindrical segment, and an upper inclined segment connected to an opposite end of the support base, the upper inclined segment including an upper lateral opening in the form of a shaft for insertion of a wrench.

9 Claims, 2 Drawing Sheets

METAL PILLAR FOR DENTAL IMPLANTS

OBJECT OF THE INVENTION

The present invention can be included in the technical field of components and elements for dental implants fitted on the upper and lower maxillaries to couple a dental cover or crown. Specifically, the object of the invention is a metal pillar which is secured to the maxillary implant in a practical and secure manner in order to avoid the loosening or detachment thereof with normal mandibular percussion or mastication.

BACKGROUND OF THE INVENTION

In the sector of dental implantology, when a patient has to have a biological dental piece replaced with an artificial dental implant, what first has to be done is to produce, by means of technical surgeries, a maxillary implant on which to secure the artificial dental implant. Therefore, the surgeon has to analyze the morphology of the maxillary of the patient in question in order to make bores in the bone, in which the maxillary implants are threaded. These maxillary implants consist of straight titanium or zirconium screws, equipped with an exterior thread and a hexagonal head in order to secure the same by means of threading to the bore made in the maxillary and with a concentric interior threading to secure the metal pillar and dental cover on the same.

Since the maxillary morphology is different for each patient, the surgeon inserts the implants at different inclinations as a function of the maxillary characteristics. Therefore, the lack of perpendicularity of the axial axes of the maxillary implants poses an alignment problem which must be solved by means of inserting aligned metal pillars of the dental covers angled for correct insertion in the assembly of the denture.

The metal pillars, both the straight and angled ones, are secured to the maxillary implant by means of a threaded screw, which passes through an axial orifice made in the metal pillar. In this way, the metal pillar is placed on the maxillary implant and the screw is tightened from the exterior by way of a shaft made in the upper base of the metal pillar. Once the metal pillar is positioned and tightened, the dental cover is put in place and is sealed so as it is immovable.

One of the drawbacks of dental implants of this type is that with time and the percussion with the mastication of the patient, the fixing screw becomes loosened, causing vibrations in the dental piece, with the consequent discomforts for the patient and even the detachment of the dental piece. Since the dental cover is sealed over the metal pillar, it is not possible to access the screw to tighten it, therefore it is necessary to break it in order to tighten it and put in place a new cover with the costs that this entails.

When the operation for tightening the screw of the metal pillar is carried out once again, deformations and limitations are observed, such as for example deformations of the hexagonal angles of the pillar; damage to the hexagonal head and the thread of the fixing screw of the pillar which cause loosening of the screw; an extremely weak screw, therefore the pressure of the adjustment thread is very limited.

Another drawback of this type of dental implant is that due to the reduced size of its components, such as the screw and hexagonal head of the implant, they become deformed, causing vibrations and the screw even breaks if it is tightened too much.

DESCRIPTION OF THE INVENTION

The present invention resolves the technical problem posed, by means of a metal pillar which includes, in a solid manner, a threaded shank which prevents it loosening.

To this end and in a more specific manner, the lower base of the metal pillar comprises a shank solidly threaded to the metal pillar itself in order to secure the same to the maxillary implant, the metal pillar of which comprises an upper opening in the form of a shaft ending internally in a hexagonal mortise for the insertion of the corresponding wrench.

In order to ensure the sealing of the metal pillar over the maxillary implant, the lower base from which the threaded shank extends comprises a frustoconical support base having an inclination matching the frustoconical support base of the maxillary implant.

On the other hand, in order to prevent oscillations of the metal pillar with respect to the maxillary implant, the threaded shank comprises a smooth cylindrical segment arranged between the frustoconical base and the threaded segment, which enters, in an adjusted manner, the interior walls of the hexagonal mortise of the maxillary implant.

In the case of the angled metal pillar, that is to say those which are used when the axial axis of the maxillary implant is not aligned with the assembly of the dentures, a system is provided in which there are a plurality of pillars in which the smooth cylindrical segments of the shanks can have different lengths or heights to determine the different end positions of the pillar, once it is fully tightened over the maxillary implant. Thus, since there are several pillars with different smooth cylindrical segment heights, it is possible to perfectly control the end position of the inclined body of the corresponding pillar, hence giving rise to different pillar varieties that cover all the correct positioning possibilities of the upper inclined segment of the pillar.

The helical screw thread of the threaded segment of the shank always starts in the same position.

In a preferred embodiment, the different helix ends determine the four or more different axial tightening end positions, one at 0°, another at 90°, another at 180° and another at 240° in order that the orthodontist can select that which is adjusted most to the correct angular position.

Since the metal pillar which is the object of the invention is one single piece, all of its parts are more robust, therefore greater tightening force can be applied. Even the hexagonal mortise can be of a greater size for using a larger tool to apply greater force. Therefore the hexagonal mortise of the interior of the shaft and the threaded shank allow a force of up to 35 N to be applied.

DESCRIPTION OF THE FIGURES

In order to complement the description and with the aim of aiding a better understanding of the characteristics of the invention, according to one preferred practical exemplary embodiment of the same, a set of drawings are attached, as an integral part of said description, in which, the following is depicted in an illustrative and non-limiting manner.

PREFERRED EMBODIMENT OF THE INVENTION

Figure 1:
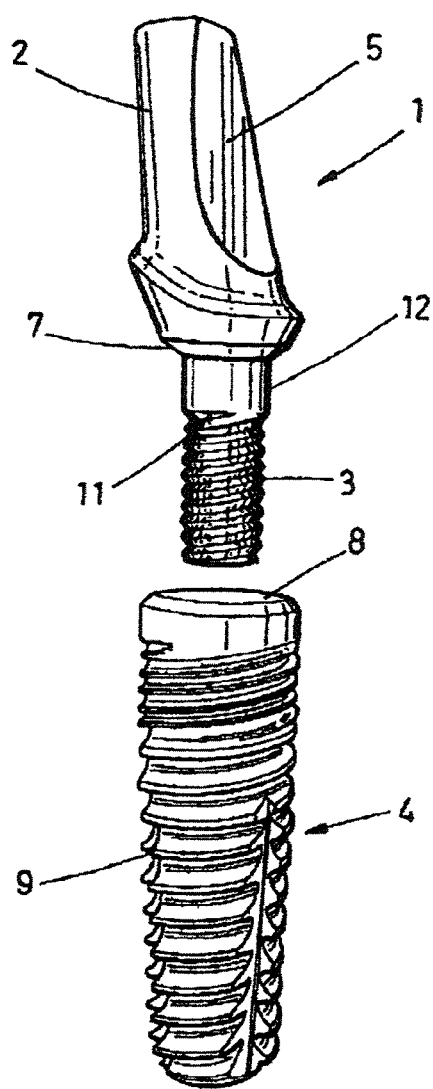
FIG. 1 shows an exploded view of the angled metal pillar which is the object of the present invention about to be fitted on the maxillary implant.

A description is given in detail below, with the aid of the FIGS. 1 to 4 previously referenced, of a preferred embodiment of the invention.

In the present preferred embodiment of the metal pillar (1), an angled metal pillar is depicted, the upper segment (2) of which is inclined for the alignment of the dental cover, not depicted in the drawings, with the assembly of the denture.

Figure 2:
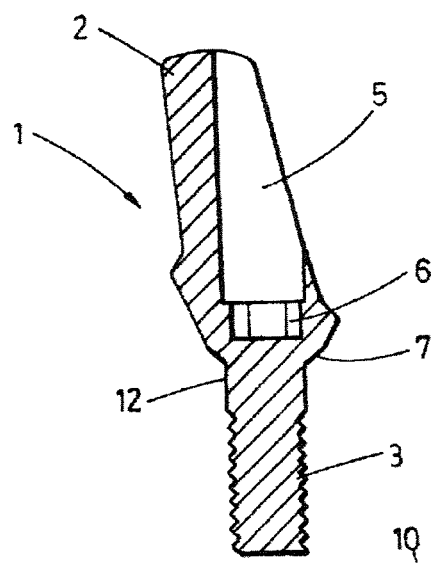
FIG. 2 shows an axial section of the angled metal pillar, in which the shank and the interior hexagonal mortise can be observed.

As can be observed in FIGS. 1 and 2, the lower base of the metal pillar (1) comprises a threaded shank (3) the helical screw thread of which starts always in the same position and forms a body that is solidly connected to the upper segment (2) of the metal pillar (1) for securing the same to the maxillary implant (4) by way of its interior thread. For the threading of the metal pillar (1) to the maxillary implant (4) previously implanted in the maxillary of the patient, an upper opening or shaft (5) is arranged in the upper segment (2), at the base of which is arranged a hexagonal mortise (6) for the insertion of the corresponding wrench. In this way, the entire metal pillar (1) is made to turn for the securing and sealing of the same on the maxillary implant (4).

In order to ensure the sealing of the metal pillar (1) against the maxillary implant (4), the lower base from which the threaded shank (3) extends, comprises a frustoconical support base (7) having an inclination matching the frustoconical support base (8) of the maxillary implant (4).

Figure 3:
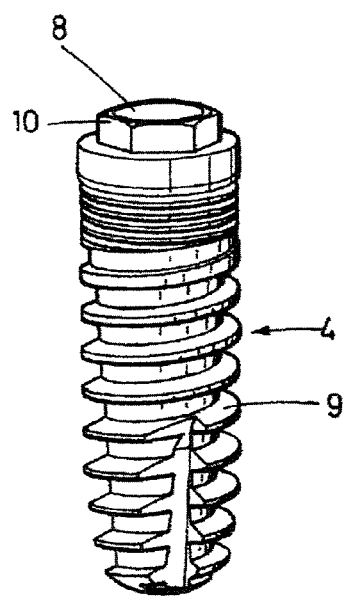
FIG. 3 shows a frontal view of a maxillary implant with exterior hexagonal head.
Figure 4:
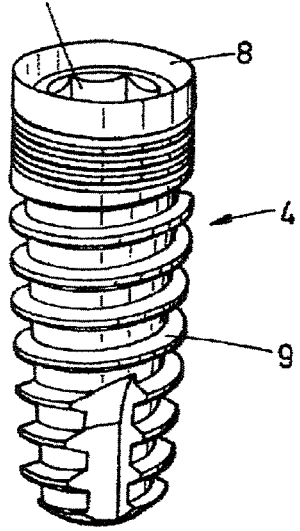
FIG. 4 shows a frontal view of a maxillary implant with interior hexagonal head.

The maxillary implants (4), as can be observed in FIGS. 3 and 4, comprise an exterior thread (9) for the securing of the same in the bone of the maxillary and a hexagonal head (10) for the insertion of the corresponding wrench, and comprise a frustoconical support base (8) having an inclination matching the frustoconical support base (7) of the metal pillar (1).

Between the frustoconical base (7) and the threaded segment of the threaded shank (3), the metal pillar (1) comprises a smooth cylindrical segment (12), with a diameter matching the axial orifice of the maxillary implant (4) to prevent oscillations. The smooth cylindrical segment adopts at least four different heights which conform at least to the four different pillar varieties so that the elected pillar for each position after being fully tightened over the implant acquires the desirable end position.

In the present exemplary embodiment, an angled metal pillar (1) has been depicted, which implies that upper part (2) thereof is inclined causing an eccentricity of the same. In order to check that said eccentricity remains in the correct position once the metal pillar (1) is tightened on the maxillary implant (4), provision is made for different metal pillars (1) to be arranged with different smooth cylindrical segment heights to determine different axial end positions of the angled metal pillar (1). For example, at least four smooth cylindrical segment heights are determined, which determine at least four different axial tightening end positions, one at 0°, another at 90°, another at 180° and another at 240° in order that the orthodontist can select the metal pillar (1) which is adjusted most to the correct angular position.

Lastly, to indicate is that the metal pillar, which is the object of the present invention, allows a greater tightening force to be applied, due to the robustness of the same. Effectively, due to the shank (3) threaded solidly to the metal pillar (1) and to the hexagonal mortise (6) with greater size, which allows the use of a more robust wrench, a tightening force of up to 35 N can be applied to the metal pillar (1).

The invention claimed is:

1. A system comprising a plurality of different one-piece, angled metal pillars for dental implants,
    each pillar comprising:
        a threaded shank having a helical thread around the shank,
        a smooth cylindrical segment having one end connected with one end of the threaded shank,
        a bevel shaped as a frustoconical support base having one end connected to an opposite end of the smooth cylindrical segment, and
        an upper inclined segment connected to an opposite end of the support base, the upper inclined segment including an upper lateral opening in the form of a shaft for insertion of a wrench; and
    the smooth cylindrical segments of the different pillars each have one of a plurality of different lengths which are different from each other and which determine abutment of the bevel against the frustoconical support base of the maxillary implant which is performed at different axial tightening end positions with respect to the maxillary implant.

2. The system, according to claim 1, wherein the bevel forms the frustoconical support base, having an inclination configured to match a frustoconical support base of a maxillary implant.

3. The system according to claim 1, wherein the different positions, obtained when the bevel of the frustoconical support base abuts against the frustoconical support base of the maxillary implant, determine with precision at least six different axial tightening end positions, which include at least one at 60°, another at 120°, another at 180°, another at 240°, another at 300° and another at 360°, which is achieved by manufacturing the pillar with variable lengths of the smooth cylindrical segment, the sequential increase or decrease of which from one of the ends has a value of 0.058 mm.

4. The system according to claim 1, wherein the lateral opening in the form of a shaft of the upper inclined segment provides access to a hexagonal mortise in an interior of the shaft which is configured to receive the wrench such that the shaft has a symmetry axis which matches exactly a symmetry axis of the threaded shank, thereby enabling to achieve a powerful and highly balanced tightening action, reaching forces that exceed at least 30 Newton without any deterioration of the pillar.

5. The system according to claim 4, wherein the forces reach 50 Newton.

6. The system according to claim 1, wherein the threaded shank and the bevel allow for universal use of the pillar with implants of hexagon, octagon and Morse taper variety.

7. The system according to claim 1, wherein the pillar has an inclination in a range between approximately 11° and 35°.

8. The system according to claim 7, wherein the pillar has an inclination of approximately 17°.

9. The system according to claim 1, wherein there are at least six different one-piece, angled metal pillars.

* * * * *